United States Patent [19]

Archer et al.

[11] 4,176,233

[45] Nov. 27, 1979

[54] STEREOSELECTIVE PREPARATION OF HEXAHYDRO DIBENZOPYRANONES AND INTERMEDIATES THEREFOR

[75] Inventors: Robert A. Archer; William A. Day, both of Indianapolis, Ind.

[73] Assignee: Eli Lilly and Company, Indianapolis, Ind.

[21] Appl. No.: 898,610

[22] Filed: Apr. 21, 1978

Related U.S. Application Data

[62] Division of Ser. No. 740,502, Nov. 10, 1976, Pat. No. 4,102,902.

[51] Int. Cl.$^2$ .............................................. C07C 69/16
[52] U.S. Cl. ..................................... 560/249; 560/107
[58] Field of Search .............................. 560/249, 256

[56] References Cited

U.S. PATENT DOCUMENTS

| | | | |
|---|---|---|---|
| 2,427,345 | 9/1947 | Bain | 560/249 |
| 2,818,427 | 12/1957 | Bain et al. | 560/249 |
| 2,834,814 | 5/1958 | Bain et al. | 560/249 |
| 3,028,418 | 4/1962 | Webb | 560/249 |
| 3,729,503 | 4/1973 | Gribou | 560/249 |
| 3,856,820 | 12/1974 | Loev | 260/345.3 |
| 3,856,821 | 12/1974 | Loev | 260/345.3 |
| 3,856,822 | 12/1974 | Loev | 260/345.3 |

OTHER PUBLICATIONS

Mechoulam et al., J. Am. Chem. Soc., 89, 4552, (1967).

*Primary Examiner*—Vivian Garner
*Attorney, Agent, or Firm*—Charles W. Ashbrook; Arthur R. Whale

[57] ABSTRACT

An optically active 4-(4-substituted-2,6-dihydroxyphenyl)-6,6-dimethyl-2-norpinanone is reacted with a protonic acid to provide an optical isomer of a cis-1-hydroxy-3-substituted-6,6-dimethyl-6,6a,7,8,10,10a-hexahydro-9H-dibenzo[b,d]pyran-9-one. Reaction of said norpinanone with a Lewis acid provides an optical isomer of trans-1-hydroxy-3-substituted-6,6-dimethyl-6,6a,7,8,10,10a-hexahydro-9H-dibenzo[b,d]pyran-9-one. The optically active norpinanones are prepared by reaction of a 5-substituted-resorcinol with an optically active 6,6-dimethyl-2,4-diacetoxy-2-norpinene or an optically active 6,6-dimethyl-2,2-diacetoxy-3-norpinene, which compounds are derived from optically active β-pinenes.

3 Claims, No Drawings

STEREOSELECTIVE PREPARATION OF HEXAHYDRO DIBENZOPYRANONES AND INTERMEDIATES THEREFOR

This is a division of application Ser. No. 740,502, filed Nov. 10, 1976, now U.S. Pat. No. 4,102,902.

BACKGROUND OF THE INVENTION

Certain 1-hydroxy-3-substituted-6,6-dimethyl-6,6a,7,8,10,10a-hexahydro-9H-dibenzo[b,d]pyran-9-ones have been found to be useful as a result of their effect on the central nervous system of mammals. A mixture of such compounds wherein the hydrogen atoms attached at the 6a- and 10a-positions are oriented trans to one another is particularly valuable in the treatment of anxiety, depression, and for providing analgesia. U.S. Pat. Nos. 3,953,603, 3,928,598 and 3,944,673 describe the use of such compounds, and draw particular attention to the use of the dl-racemic mixture of trans-1-hydroxy-3-(1,1-dimethylheptyl)-6,6-dimethyl-6,6a,7,8,10,10a-hexahydro-9H-dibenzo[b,d]pyran-9-one, now generically referred to as Nabilone.

It recently has been discovered that separation of the dl-racemic mixture of both cis- and trans-isomers of the aforementioned hexahydrodibenzopyranones into the corresponding optically active isomers provides compounds with varying biological properties. In particular, one of the optical isomers of both cis and trans-hexahydrodibenzopyranones appears to be more active than the other optical isomer in its effect on the central nervous system of mammals. An object of this invention is thus to provide a process for preparing optically active isomers of certain cis- and trans-1-hydroxy-3-substituted-6,6-dimethyl-6,6a,7,8,10,10a-hexahydro-9H-dibenzo[b,d]pyran-9-ones. A further object of the invention is to provide certain new compounds which are useful as intermediates in the preparation of such optically active hexahydrodibenzopyranones.

SUMMARY OF THE INVENTION

This invention relates to a process for stereo-selectively preparing optical isomers of 6a,10a-cis, and 6a,10a-trans-hexahydrodibenzopyranones, and to intermediates useful in such process. More particularly, the invention provides optically active 6,6-dimethyl-2,4-diacetoxy-2-norpinene and optically active 6,6-dimethyl-2,2-diacetoxy-3-norpinene, which compounds can be represented by the general formula

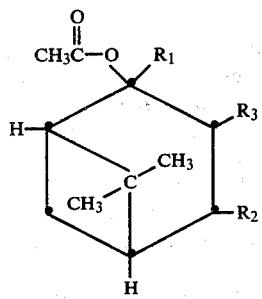

wherein $R_1$ is acetoxy, or taken with $R_3$, forms a double bond; $R_2$ is acetoxy or, taken with $R_3$, forms a double bond; and $R_3$, taken with $R_1$ forms a double bond, or taken with $R_2$ forms a double bond. It will of course be seen that when one of $R_1$ or $R_2$ is acetoxy, the other, taken with $R_3$, forms a double bond, and that $R_1$ and $R_2$ both are not acetoxy.

This invention additionally encompasses optically active isomers of a compound of the formula

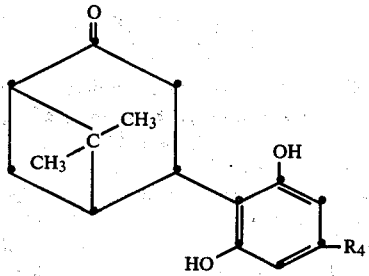

wherein $R_4$ is $C_5$–$C_{10}$ alkyl, $C_5$–$C_{10}$ alkenyl, $C_5$–$C_8$ cycloalkyl or $C_5$–$C_8$ cycloalkenyl. Preferred compounds are those having the above formula when $R_4$ is $C_5$–$C_{10}$ alkyl, particularly 1,1-dimethylheptyl.

The invention also provides a process for preparing an optical isomer of a compound having the formula

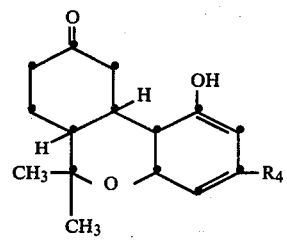

wherein $R_4$ is $C_5$–$C_{10}$ alkyl, $C_5$–$C_{10}$ alkenyl, $C_5$–$C_8$ cycloalkyl, or $C_5$–$C_8$ cycloalkenyl; comprising reacting an optically active compound of the formula

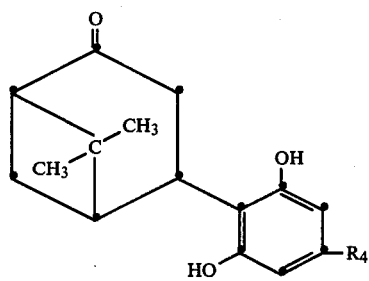

wherein $R_4$ has the above-defined meaning, with an acid in an unreactive organic solvent.

A preferred process of this invention comprises reacting an optically active 4-(4-substituted-2,6-dihydroxyphenyl)-6,6-dimethyl-2-norpinanone with a protonic acid in an unreactive organic solvent to provide an optical isomer of a 6a,10a-cis-1-hydroxy-3-substituted-6,6-dimethyl-6,6a,7,8,10,10a-hexahydro-9H-dibenzo[b,d]pyran-9-one.

A further preferred process as contemplated by this invention comprises reacting an optically active 4-(4-substituted-2,6-dihydroxyphenyl)-6,6-dimethyl-2-norpinanone with a Lewis acid in an unreactive organic solvent to provide an optical isomer of a 6a,10a-trans-1-hydroxy-3-substituted-6,6-dimethyl-6,6a,7,8,10,10a-hexahydro-9H-dibenzo[b,d]pyran-9-one. A particularly preferred group of Lewis acids include stannic chloride, boron trifluoride and aluminum chloride. An especially preferred process comprises reacting a (+)-4-[4-(C₅–C₁₀ alkyl)-2,6-dihydroxyphenyl]-6,6-dimethyl-2-norpinanone with stannic chloride to provide the corresponding (−)-trans-1-hydroxy-3-(C₅–C₁₀ alkyl)-6,6-dimethyl-6,6a,7,8,10,10a-hexahydro-9H-dibenzo[b,d]-pyran-9-one.

DETAILED DESCRIPTION OF THE INVENTION

As used throughout this specification and in the appended claims, R₄ is defined as C₅–C₁₀ alkyl, C₅–C₁₀ alkenyl, C₅–C₈ cycloalkyl; and C₅–C₈ cycloalkenyl. The term "C₅–C₁₀ alkyl" refers to both straight and branched carbon chains, examples of which include n-pentyl, n-hexyl, n-octyl, n-heptyl, n-decyl, 1-methylpentyl, 1-methylhexyl, 1,2-dimethylhexyl, 1,1-dimethylheptyl, 1,1-diethylpentyl, 1,2,3-trimethylheptyl, 2-ethylhexyl, 3-propylpentyl, 1,3-dimethyloctyl, 2,2-dimethyloctyl, 2,3-dimethylpentyl, and related groups.

Examples of "C₅–C₁₀ alkenyl" groups include 2-pentenyl, 3-hexenyl, 4-octenyl, 5-decenyl, 1,2-dimethyl-1-heptenyl, 1,1-dimethyl-2-heptenyl, 1-ethyl-3-hexenyl, 3,4-dimethyl-3-hexenyl, 3-ethyl-4-heptenyl, and related groups.

Typical examples of groups designated by the term "C₅–C₈ cycloalkyl" include cyclopentyl, cyclohexyl, cycloheptyl, and cyclooctyl. Similarly, typical "C₅–C₈ cycloalkenyl" groups include 1-cyclopentenyl, 2-cyclohexenyl, 2-cycloheptenyl, and 3-cyclooctenyl.

In accordance with this invention, the optically active norpinene starting materials of the formula

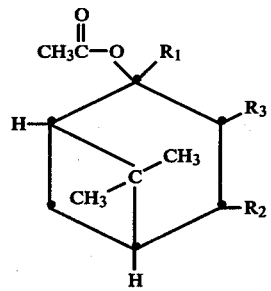

in which R₁, R₂ and R₃ have the above-defined meanings, are produced by reacting an optically active nopinone enol acetate of the formula

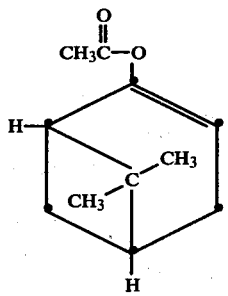

with lead tetraacetate. The optically active nopinone enol acetates of the above formula are readily available by the method of Coxon et al. *Aust. J. Chem.*, 23, 1069 (1970). Such compounds are derived from the respective optically active d and l isomers of β-pinene. The norpinene derivatives of this invention are prepared by reacting the above-noted nopinone enol acetate with an excess of lead tetraacetate in an organic solvent such as benzene. The lead tetraacetate generally is utilized in about 2 to 10 molar excess, although larger excesses can be used if desired. The reaction normally is carried out at about 50° to 100° C., and the length of reaction determines which product is obtained. When the reaction is terminated after about 1 to 3 hours, the product isolated is an optically active isomer of 6,6-dimethyl-2,2-diacetoxy-3-norpinene, wherein R₁ is acetoxy and R₂ and R₃ together form a double bond. When the reaction is allowed to continue for about 16 to 20 hours, the product formed is an optical isomer of 6,6-dimethyl-2,4-diacetoxy-2-norpinene, wherein R₁ together with R₃ is a double bond, and R₂ is acetoxy. In either case, the product of the reaction is isolated by filtering the reaction mixture and distilling the filtrate. It should of course be realized that esters or ethers other than the aforementioned enol acetates can be utilized as a starting material, for instance nopinone enol formates or benzoates; however, the norpinene derivatives which are then formed are mixed esters, such as a 2-benzoyloxy-2-acetoxy-norpinene derivative for instance. It is therefore more convenient to utilize the aforementioned nopinone enol acetates as the starting materials.

The optically pure isomers of 6,6-dimethyl-2,4-diacetoxy-2-norpinene and 6,6-dimethyl-2,2-diacetoxy-3-norpinene are next reacted with a 5-substituted resorcinol to provide, either directly, an optically pure hexahydrodibenzopyranone, or preferably to provide an optically pure 4-(4-substituted-b 2,6-dihydroxyphenyl)-6,6-dimethyl-2-norpinanone, which is subsequently converted to a hexahydrodibenzopyranone. More particularly, reaction of either of the aforementioned 2,2-diacetoxynorpinene derivative or the 2,4-diacetoxynorpinene derivative, as the optically pure d or l isomers, with a 5-substituted resorcinol, in the presence of a protonic acid and at a temperature of about 0° to 30° C. affords, after about 2 to 4 hours, an optically pure 4-(4-substituted-2,6-dihydroxyphenyl)-6,6-dimethyl-2-norpinanone of the general formula

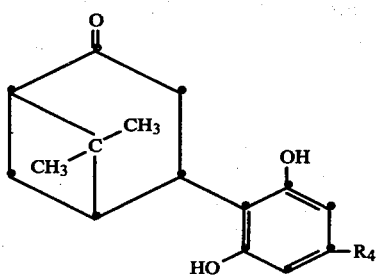

in which R₄ has the above-defined meaning. When reference is made herein to optical purity, regarding compounds of the above formula, it is only intended to refer to the stereochemistry of the norpinanone portion of the molecule, and no designation of stereochemistry of the group defined by R₄ is intended. Accordingly, when R₄ is a group possessing asymmetric centers, no resolution of the possible stereoisomers attributable thereto is comprehended herein.

The condensation reaction between a 2,2-diacetoxynorpinene derivative or a 2,4-diacetoxynorpinene derivative and a resorcinol is accomplished by commingling approximately equimolar quantities of such reactants in the presence of approximately an equimolar quantity of a protonic acid such as hydrochloric acid, sulfuric acid, phosphoric acid, para-toluenesulfonic acid, para-bromotoluene-sulfonic acid, and the like. The reaction is best carried out in an unreactive organic solvent. Any of a number of such solvents can be utilized, including halogenated hydrocarbons such as chloroform, dichloromethane, chloroethane, 1,2-dichloroethane, 1,1-dibromomethane; aromatics such as benzene, toluene, chlorobenzene, m-xylene, p-xylene, and the like. The reaction preferably is carried out at a temperature of about 20° to 30° C., and usually is substantially complete within about 2 to about 4 hours. As a typical example, about equimolar quantities of an optically pure norpinene derivative such as d-6,6-dimethyl-2,2-diacetoxy-3-norpinene, and a 5-substituted resorcinol such as 5-n-pentylresorcinol are commingled in a common unreactive organic solvent such as benzene, and the solution is stirred at 25° C. for 4 hours in the presence of an equimolar quantity of a protonic acid such as sulfuric acid. The product of such reaction is an optically pure isomer of 4-(4-n-pentyl-2,6-dihydroxyphenyl)-6,6-dimethyl-2-norpinanone. Such compounds are readily isolated by simply washing the reaction mixture with a mild base, such as sodium bicarbonate, and removing the reaction solvent. The 4-(4-substituted-2,6-dihydroxyphenyl)-6,6-dimethyl-2-norpinanones so produced typically exist as highly crystalline solids which are readily purified further if needed by routine procedures, such as recrystallization from solvents such as benzene, hexane, cyclohexane, octane, and related solvents.

Examples of typically prepared optically active 4-(4-substituted-2,6-dihydroxyphenyl)-6,6-dimethyl-2-norpinanones include:

(+)-4-(4-n-octyl-2,6-dihydroxyphenyl)-6,6-dimethyl-2-norpinanone;
(−)-4-(4-(1-methylhexyl)-2,6-dihydroxyphenyl)-6,6-dimethyl-2-norpinanone;
(−)-4-(4-(1,2-dimethylbutyl)-2,6-dihydroxyphenyl)-6,6-dimethyl-2-norpinanone;
(+)-4-(4-(3-hexenyl)-2,6-dihydroxyphenyl)-6,6-dimethyl-2-norpinanone;
(+)-4-(4-(4-nonenyl)-2,6-dihydroxyphenyl)-6,6-dimethyl-2-norpinanone;
(−)-4-(4-cyclohexyl-2,6-dihydroxyphenyl)-6,6-dimethyl-2-norpinanone;
(−)-4-(4-cyclooctyl-2,6-dihydroxyphenyl)-6,6-dimethyl-2-norpinanone;
(+)-4-[4-(3-cyclohexenyl)-2,6-dihydroxyphenyl]-6,6-dimethyl-2-norpinanone;
(+)-4-[4-(1-cycloheptenyl)-2,6-dihydroxyphenyl]-6,6-dimethyl-2-norpinanone; and related compounds.

The 4-(4-substituted-2,6-dihydroxyphenyl)-6,6-dimethyl-2-norpinanones so produced are next converted to optically active isomers of either 6a,10a-cis-1-hydroxy-3-substituted-6,6-dimethyl-6,6a,7,8,10,10a-hexahydro-9H-dibenzo[b,d]pyran-9-ones or 6a,10a-trans-1-hydroxy-3-substituted-6,6-dimethyl-6,6a,7,8,10,10a-hexahydro-9H-dibenzo[b,d]pyran-9-ones. More specifically, either the d or the l optical isomer of a 4-(4-substituted-2,6-dihydroxyphenyl)-6,6-dimethyl-2-norpinanone can be reacted with about an equimolar quantity of a protic acid such as hydrochloric acid, sulfuric acid, para-toluenesulfonic acid, or the like, in an unreactive organic solvent, at a temperature from about 30° to about 80° C. for a period of time from about 12 to about 36 hours, to provide an optically active d or l isomer of the corresponding 6a,10a-cis-1-hydroxy-3-substituted-6,6-dimethyl-6,6a,7,8,10,10a-hexahydro-9H-dibenzo[b,d]pyran-9-one. Solvents commonly utilized include halogenated hydrocarbons such as chloroform, dichloromethane, 1,2-dibromoethane, and chloropropane, as well as aromatic solvents such as benzene, toluene, chlorobenzene, xylene, and the like. The reaction generally is conducted at a temperature within the range of from about 30° to about 80° C., and preferably is simply carried out at the reflux temperature of the reaction mixture. The product of such reaction is substantially a 6a,10a-cis-hexahydrodibenzopyranone, as an optically active isomer; however, minor quantities of the corresponding 6a,10a-trans-hexahydrodibenzopyranone usually can be detected. The reaction product is readily isolated by simply washing the reaction free of any remaining acid, for example by washing the organic solution with a base such as aqueous sodium bicarbonate, and then removing the reaction solvent. Purification of the product so formed can be accomplished by standard chromatographic techniques, which generally effects separation of any 6a,10a-cis-hexahydrodibenzopyranone from any of the 6a,10a-trans derivative.

Reaction of either the d or l optical isomer of a 4-(4-substituted-2,6-dihydroxyphenyl)-6,6-dimethyl-2-norpinanone with a Lewis acid in an unreactive organic solvent provides the corresponding d or l optical isomer of a 6a,10a-trans-1-hydroxy-3-substituted-6,6-dimethyl-6,6a,7,8,10,10a-hexahydro-9H-dibenzo[b,d]pyran-9-one. Commonly used Lewis acids include stannic chloride, boron trifluoride, generally as the commercially available diethyl etherate complex, aluminum chloride, and the like. Stannic chloride is an especially preferred Lewis acid for the reaction. The conversion of the norpinanone derivative to the corresponding 6a,10a-trans-hexahydro-dibenzopyranone generally is accomplished by reacting the norpinanone with from about 1 to 10 molar excess of a Lewis acid, preferably from about 1 to 3 molar excess. The reaction is carried out in any of a number of commonly used unreactive organic solvents, examples of which include halogenated hydrocarbons such as chloroform, dichloromethane, bromoethane, and 1,2-dibromoethane, and aromatic solvents such as benzene, toluene, xylene, and the like. The reaction normally is carried out at a temperature of from about 0° to about 30° C., and usually is substantially complete within about 8 to about 24 hours. The product is readily isolated by simply washing the reaction mixture with an aqueous acid such as dilute hydrochloric acid, and with a dilute aqueous base, and then removing the solvent, for instance by evaporation. The product so formed is predominantly an optically active d or l isomer of a 6a,10a-trans-1-hydroxy-3-substituted-6,6-dimethyl-6,6a,7,8,10,10a-hexahydro-9H-dibenzo[b,d]pyran-9-one, with minor quantities of the corresponding optically active 6a,10a-cis-derivative present. Chromatography generally effects purification so as to cleanly afford the optically active 6a,10a-trans-hexahydrodibenzopyranone. However, if desired, any 6a,10a-cis-hexahydrodibenzopyranone can be converted to the corresponding 6a,10a-trans isomer simply by reaction with aluminum chloride. The 6a,10a-cis-hexahydrodibenzopyranones, in addition to being pharmacologically active in themselves, additionally serve as intermediates leading to the somewhat more active 6a,10a-trans isomers. The l-isomers of such 6a,10a-trans isomers are of particular importance in the treatment of depression and anxiety. The d-isomers of such 6a,10a-trans isomers are especially valuable as intermediates. For example, the d isomer of trans-1-hydroxy-3-(1,1-dimethylheptyl)-6,6-dimethyl-6,6a,7,8,10,10a-hexahydro-9H-dibenzo[b,d]pyran-9-one can be reduced at the 9-ketone moiety to provide the corresponding d-trans-1,9R-dihydroxy-3-(1,1-dimethylheptyl)-6,6-dimethyl-6,6a,7,8,10,-10a-hexahydro-9H-dibenzo[b,d]pyran, which compound is valuable due to its effect on the central nervous system of mammals, as demonstrated by standard mouse activity assays.

As has already been pointed out, isolation of the 4-(4-substituted-2,6-dihydroxyphenyl)-6,6-dimethyl-2-norpinanones is not absolutely required since the optically active 6,6-dimethyl-2,4-diacetoxy-3-norpinenes and 6,6-dimethyl-2,2-diacetoxy-2-norpinenes can be converted in one step to either an optically active cis-1-hydroxy-3-substituted-6,6-dimethyl-6,6a,7,8,10,10a-hexahydro-9H-dibenzo[b,d]pyran-9-one or an optically active 6a,10a-trans-hexahydrodibenzopyranone. In particular, reaction of a 2,4-diacetoxy-3-norpinene derivative or a 2,2-diacetoxy-2-norpinene derivative with a 5-substituted resorcinol in the presence of a protonic acid such as para-toluenesulfonic acid, and in an unreactive organic solvent such as chloroform, for a period of time of about 12 to 36 hours and at an elevated temperature of about 30° to about 80° C., provides directly an optically active cis-1-hydroxy-3-substituted-6,6-dimethyl-6,6a,7,8,10,-10a-hexahydro-9H-dibenzo[b,d]pyran-9-one. Similarly, reaction of an optically active 2,4-diacetoxy-3-norpinanone or 2,2-diacetoxy-2-norpinanone with a 5-substituted resorcinol in the presence of a Lewis acid such as boron trifluoride, and in an unreactive organic solvent such as chloroform, at a temperature of about 0° to about 30° C. for 8 to 16 hours, provides an optically active trans-1-hydroxy-3-substituted-6,6-dimethyl-6,6a,7,8,10,10a-hexahydro-9H-dibenzo[b,d]pyran-9-one.

While the aforementioned norpinanone derivatives can, by proper selection of reaction conditions, be converted directly to optically active 6a,10a-cis- and 6a,10a-trans-hexahydrodibenzopyranones, it is believed that such reactions proceed in each instance through the optically active 4-(4-substituted-2,6-dihydroxyphenyl)-6,6-dimethyl-2-norpinanones which were described hereinabove. According to this invention, it is preferred to carry out the reaction between the diacetoxynorpinene derivatives and a 5-substituted resorcinol in such a way that the norpinanone intermediate is formed, thus permitting its isolation and purification, and subsequent conversion to a hexahydrodibenzopyranone. Such preferred process obviates the need for more extensive purification of the hexahydrodibenzopyranones which are produced directly from the diacetoxynorpinenes, since in such direct conversion minor quantities of terpene impurities generally are present and are somewhat difficult to remove from the desired product.

As was hereinbefore pointed out, certain hexahydrodibenzopyranones which have been found to be useful in causing analgesia in mammals, and in the treatment of anxiety, depression, and similar conditions connected with the central nervous system. While cis-1-hydroxy-3-substituted-6,6-dimethyl-6,6a,7,8,10,10a-hexahydro-9H-dibenzo[b,d]pyran-9-one, as the dl racemic mixture, is useful pharmacologically in and of itself, the corresponding dl-trans isomers normally are somewhat more potent biologically. The separate d and l optical isomers of such 6a,10a-cis and 6a,10a-trans-hexahydrodibenzopyranones, as prepared according to the process of this invention, are useful either in the treatment of anxiety and depression, or as intermediates. The separate pharmacologically active optical isomers of such cis and trans-hexahydrodibenzopyranones which are prepared according to the process of this invention accordingly are used in the same manner as are the corresponding racemic mixtures which are described in the aforementioned references.

In an effort to more fully illustrate certain aspects of this invention, the following detailed examples are provided. Such examples are not intended to be limiting in any way and should not be so construed.

EXAMPLE 1

(−)-6,6-Dimethyl-2,4-diacetoxy-2-norpinene

To a stirred solution under a nitrogen gas atmosphere of 18.0 g. of (−)-nopinone enol acetate dissolved in 250 ml. of dry benzene was added in one portion 48.8 g. of lead tetraacetate which had been dried over phosphorous pentoxide and potassium hydroxide. The reaction mixture was heated to reflux and stirred for eighteen hours. The reaction mixture then was cooled to room temperature, filtered, and the filtrate was washed with ten percent aqueous sodium bicarbonate solution and with water, dried, and the solvent was removed therefrom by evaporation under reduced pressure to provide 23.5 g. of the crude product as a clear liquid. The product so formed was distilled to provide 9.3 g. of (−)-6,6-dimethyl-2,4-diacetoxy-2-norpinene. B.P. 115°–118° C. at 5 torr. $[\alpha]^{20}D - 89.7°$ (c=1.0, CHCl$_3$).

H$^1$ nmr (CDCl$_3$)
$\delta$ 5.25 (m, 2H)
$\delta$ 2.4 (m, 4H)
$\delta$ 2.1 (s, 3H)
$\delta$ 2.0 (s, 3H)
$\delta$ 1.35 (s, 3H)
$\delta$ 1.0 (s, 3H)

IR (CHCl$_3$): 1370, 1763 cm$^{-1}$, carbonyl. mass spectrum m/e: 196 (M$^+$ —CH$_2$=C=O).

EXAMPLE 2

(+)-6,6-Dimethyl-2,2-diacetoxy-3-norpinene

To a stirred solution under a nitrogen gas atmosphere of 18.0 g. of (−)-nopinone enol acetate dissolved in 250 ml. of dry benzene was added in one portion 48.8 g. of lead tetraacetate which had been dried over phosphorus pentoxide and potassium hydroxide. The reaction mixture was heated to reflux and stirred for two hours. The mixture then was cooled to room temperature, washed with aqueous sodium bicarbonate solution and with water, dried, and the solvent was removed by evaporation under reduced pressure to provide the product as an oil. The oil was then distilled to provide 9.8 g. of (+)-6,6-dimethyl-2,2-diacetoxy-3-norpinene. B.P. 102°–103° C. at 5 torr. $[\alpha]^{20}D + 33.2°$ (c=1.0, CHCl$_3$).

Analysis Calc. for C$_{13}$H$_{18}$O$_4$: Theory: C, 65.53; H, 7.61; COCH$_3$, 36.12. Found: C, 65.77; H, 7.32; COCH$_3$, 36.56.

H$^1$ nmr (CDCl$_3$)
$\delta$ 6.4 (m, 2H)
$\delta$ 3.15 (m, 1H)
$\delta$ 2.3 (m, 3H)
$\delta$ 2.1 (s, 6H)
$\delta$ 1.4 (s, 3H)
$\delta$ 1.1 (s, 3H)

mass spectrum m/e: 196 (M$^+$ —42). IR (CHCl$_3$) 1750 cm$^{-1}$, carbonyl.

EXAMPLE 3

(+)-4-[4-(1,1-Dimethylheptyl)-2,6-dihydroxyphenyl]-6,6-dimethyl-2-norpinanone

A solution of 1.18 g. of (−)-6,6-dimethyl-2,4-diacetoxy-2-norpinene in 50 ml. of chloroform containing 0.95 g. of para-toluenesulfonic acid mono-hydrate stood at about 25° C. for four hours. The reaction mixture was then diluted with 100 ml. of diethyl ether, and the resulting solution was washed with ten percent aqueous sodium bicarbonate solution, with water, dried, and the solvent was removed therefrom by evaporation under reduced pressure to provide the product as a semi-crystalline solid. The product so formed was triturated with 25 ml. of n-hexane and filtered, thus affording 1.30 g. of (+)-4-[4-(1,1-dimethylheptyl)-2,6-dihydroxyphenyl]-6,6-dimethyl-2-norpinanone. M.P. 171°–174° C. $[\alpha]^{20}D + 55.8°$ (C=1.0 CHCl$_3$)

Analysis Calc. for $C_{24}H_{36}O_3$: Theory: C, 77.38; H, 9.74. Found: C, 77.59; H, 9.83.

H$^1$ nmr (CDCl$_3$+DMSO$_{d6}$)

$\delta$ 8.05 (s, 2H, phenolic OH)
$\delta$ 6.35 (s, 2H)
$\delta$ 4.05 (t, 1H)
$\delta$ 3.65 (m, 1H)
$\delta$ 2.45 (m, 5H)
$\delta$ 1.35 (s, 3H)
$\delta$ 1.15 (m, 19H)
$\delta$ 0.95 (s, 3H)

IR (KBr) 1668 cm$^{-1}$, carbonyl. mass spectrum m/e: 372 (M$^+$).

Following the same procedure, 1.18 g. of (+)-6,6-dimethyl-2,2-diacetoxy-3-norpinene was converted to (+)-4-[4-(1,1-dimethylheptyl)-2,6-dihydroxyphenyl]-6,6-dimethyl-2-norpinanone having the identical physical properties as that obtained as described in Example 3.

EXAMPLE 4

(−)-cis-1-Hydroxy-3-(1,1-dimethylheptyl)-6,6-dimethyl-6,6a,7,8,10,10a-hexahydro-9H-dibenzo[b,d]pyran-9-one A solution of 372 mg. of (+)-4-[4-(1,1-dimethylheptyl)-2,6-dihydroxyphenyl]-6,6-dimethyl-2-norpinanone, from Example 3, dissolved in 25 ml. of chloroform containing 190 ml. of para-toluenesulfonic acid monohydrate was heated to reflux and stirred for twenty four hours. The reaction mixture then was cooled to room temperature, diluted with 25 ml. of water, and extracted several times with 25 ml. portions of diethyl ether. The ethereal extracts were combined, washed with ten percent aqueous sodium bicarbonate solution and with water, dried, and the solvent was removed therefrom by evaporation under reduced pressure to provide 380 mg. of the product as a white foam. The crude product so formed was chromatographed over a column packed with commercial Woelm activity II silica gel, eluting with five percent diethyl ether in benzene. Evaporation of the solvent from the appropriate fractions afforded 228 mg. of (−)-cis-1-hydroxy-3-(1,1-dimethylheptyl)-6,6-dimethyl-6,6a,7,8,10,10a-hexahydro-9H-dibenzo[b,d]pyran-9-one. M.P. 139.5°–141° C. $[\alpha]^{20}D - 50.0°$ (c=1.0, CHCl$_3$), mass spectrum m/e: calc. for $C_{24}H_{36}O_3$, 372.2664; found 372.2665.

EXAMPLE 5

(−)-trans-1-Hydroxy-3-(1,1-dimethylheptyl)-6,6-dimethyl-6,6a,7,8,10,10a-hexahydro-9H-dibenzo[b,d]pyran-9-one To a solution of 372 mg. of (+)-4-[4-(1,1-dimethylheptyl)-2,6-dihydroxyphenyl]-6,6-dimethyl-2-norpinanone in 25 ml. of chloroform was added in one portion 1.0 ml. of stannic chloride. The reaction mixture was stirred at 25° C. for sixteen hours, and then added to 50 g. of ice. The aqueous reaction mixture was extracted several times with 25 ml. portions of diethyl ether, and the ethereal extracts were then combined, washed with 2 N hydrochloric acid solution and then with five percent aqueous sodium bicarbonate solution. The organic layer next was washed with water, dried, and the solvent was removed by evaporation under reduced pressure to provide 378 mg. of the product as a crude foam. The foam was next chromatographed over a Woelm activity II silica gel column, eluting with benzene. Evaporation of the solvent from the fractions shown by thin layer chromatography to contain one component afforded 305 mg. of (−)-trans-1-hydroxy-3-(1,1-dimethylheptyl)-6,6-dimethyl-6,6a,7,8,10,10a-hexahydro-9H-dibenzo[b,d]pyran-9-one.

$[\alpha]^{20}D - 52.3°$ (c=1.0, CHCl$_3$), mass spectrum calc. for $C_{24}H_{36}O_3$ 372.2664, m/e found 372.2667.

Evaporation of the solvent from eluates shown by thin layer chromatography to contain a different component afforded 55 mg. of (−)-cis-1-hydroxy-3-(1,1-dimethylheptyl)-6,6-dimethyl-6,6a,7,8,10,10a-hexahydro-9H-dibenzo[b,d]pyran-9-one. $[\alpha]^{20}D - 50°$ (c=1.0, CHCl$_3$).

EXAMPLE 6

(−)-trans-1-Hydroxy-3-(1,1-dimethylheptyl)-6,6-dimethyl-6,6a,7,8,10,10a-hexahydro-9H-dibenzo[b,d]pyran-9-one A solution of 77 mg. of (−)-cis-1-hydroxy-3-(1,1-dimethylheptyl)-6,6-dimethyl-6,6a,7,8,10,10a-hexahydro-9H-dibenzo[b,d]pyran-9-one in 5 ml. of dichloromethane containing 77 mg. of aluminum chloride was stirred at 25° C. for four hours. The reaction mixture was then diluted with 20 g. of ice, and the resulting aqueous mixture was extracted with diethyl ether. The ethereal extracts were combined, washed with 2 N hydrochloric acid and with ten percent aqueous sodium bicarbonate solution, and then washed with water, dried, and the solvent was removed by evaporation under reduced pressure to provide 75 mg. of the product as an oil. The oil so formed was chromatographed over a thick layer silica gel coated plate. Elution of the principle band with a twenty percent solution of ethyl acetate in benzene, and evaporation of the solvent therefrom, afforded 54 mg. of (−)-trans-1-hydroxy-3-(1,1-dimethylheptyl)-6,6-dimethyl-6,6a,7,8,10,10a-hexahydro-9H-dibenzo[b,d]pyran-9-one. $[\alpha]^{60}D - 53.8°$ (c=1.0, CHCl$_3$).

EXAMPLE 7

(−)-trans-1-Hydroxy-3-(1,1-dimethylheptyl)-6,6-dimethyl-6,6a,7,8,10,10a-hexahydro-9H-dibenzo[b,d]pyran-9-one A mixture of 2.38 g. of (−)-6,6-dimethyl-2,4-diacetoxy-2-norpinene and 2.76 g. of 5-(1,1-dimethylheptyl)-resorcinol dissolved in 50 ml. of dichloromethane containing 10.2 g. of boron trifluoride diethyl etherate was cooled to 0° C. in an ice bath and stirred for one hour. The reaction mixture then was warmed to 25° C. and stirred for an additional twelve hours. The reaction mixture next was poured into 25 g. of ice, and the resulting aqueous mixture was extracted with diethyl ether. The organic layer was separated, washed with ten percent aqueous sodium bicarbonate solution, dried, and the solvent was removed therefrom by evaporation under reduced pressure to provide 4.1 g. of a brown oil. The oil so formed was purified by chromatography over a column packed with Woelm Activity II silica gel, eluting with benzene. The appropriate fractions, shown by thin layer chromatography to contain the desired product, were combined and the solvent was evaporated therefrom to afford 1.06 g. of (−)-trans-1-hydroxy-3-(1,1-dimethylheptyl)-6,6-dimethyl-6,6a,7,8,10,10a-hexahydro-9H-dibenzo[b,d]pyran-9-one as a colorless oil. $[\alpha]^{20}D - 47.5°$ (c=1.0, CHCl$_3$).

Following the same procedure as set forth above, (+)-6,6-dimethyl-2,2-diacetoxy-3-norpinene was reacted with 5-(1,1-dimethylheptyl)resorcinol in the presence of boron trifluoride diethyl etherate to afford (−)-trans-1-hydroxy-3-(1,1-dimethylheptyl)-6,6-dimethyl-6,6a,7,8,10,10a-hexahydro-9H-dibenzo[b,d]pyran-9-one.

We claim:
1. A compound of the formula

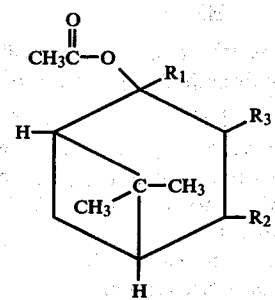

wherein:
$R_1$ is acetoxy or, taken together with $R_3$, forms a double bond;
$R_2$ is acetoxy or, taken together with $R_3$, forms a double bond; and
$R_3$, taken together with $R_1$ or with $R_2$, forms a double bond, provided that when one of $R_1$ or $R_2$ is acetoxy, the other, taken with $R_3$, forms a double bond, and that $R_1$ and $R_2$ both are not acetoxy.

2. The compound of claim 1 wherein $R_1$ is acetoxy and $R_2$ and $R_3$ together form a double bond.

3. The compound of claim 1 wherein $R_2$ is acetoxy and $R_1$ and $R_3$ together form a double bond.

* * * * *